United States Patent
Wu et al.

(10) Patent No.: US 9,949,714 B2
(45) Date of Patent: Apr. 24, 2018

(54) METHOD, ELECTRONIC APPARATUS, AND COMPUTER READABLE MEDIUM OF CONSTRUCTING CLASSIFIER FOR DISEASE DETECTION

(71) Applicant: HTC Corporation, Taoyuan (TW)

(72) Inventors: Meng-Hsi Wu, Taoyuan (TW); Edward Chang, Taoyuan (TW)

(73) Assignee: HTC Corporation, Taoyuan (TW)

( * ) Notice: Subject to any disclaimer, the term of this patent is extended or adjusted under 35 U.S.C. 154(b) by 0 days.

(21) Appl. No.: 15/220,398

(22) Filed: Jul. 27, 2016

(65) Prior Publication Data

US 2017/0032221 A1     Feb. 2, 2017

Related U.S. Application Data

(63) Continuation-in-part of application No. 14/857,820, filed on Sep. 18, 2015.

(60) Provisional application No. 62/198,145, filed on Jul. 29, 2015.

(51) Int. Cl.
| | |
|---|---|
| *G06K 9/00* | (2006.01) |
| *A61B 7/04* | (2006.01) |
| *G06K 9/62* | (2006.01) |
| *A61B 5/0402* | (2006.01) |
| *A61B 5/00* | (2006.01) |

(52) U.S. Cl.
CPC .............. *A61B 7/04* (2013.01); *A61B 5/0402* (2013.01); *A61B 5/7267* (2013.01); *G06K 9/629* (2013.01); *G06K 9/6263* (2013.01); *G06K 9/6269* (2013.01); *G06K 9/6292* (2013.01)

(58) Field of Classification Search
None
See application file for complete search history.

(56) References Cited

U.S. PATENT DOCUMENTS

| | | | | |
|---|---|---|---|---|
| 7,454,046 | B2 * | 11/2008 | Chhibber | A61B 5/442 382/118 |
| 7,916,910 | B2 * | 3/2011 | Cotton | A61B 5/0059 382/128 |
| 7,945,314 | B1 * | 5/2011 | Snell | A61B 5/0006 600/510 |
| 8,073,212 | B2 * | 12/2011 | Gerlach | A61B 5/0088 382/128 |
| 8,131,029 | B2 * | 3/2012 | Chhibber | G06K 9/00288 382/118 |
| 8,433,116 | B2 * | 4/2013 | Butler | G06F 19/321 382/128 |

(Continued)

OTHER PUBLICATIONS

Zheng et al, Time Series Classification Using Multi-Channels Deep Convolutional Neural Networks, WAIM 2014, LNCS 8485, pp. 298-310, 2014.*

(Continued)

*Primary Examiner* — Andrae S Allison
(74) *Attorney, Agent, or Firm* — JCIPRNET

(57) ABSTRACT

The disclosure provides a method, an electronic apparatus, and a computer readable medium of constructing a classifier for disease detection. The method includes the following steps. A codebook of representative features is constructed based on a plurality of disease-irrelevant data. Transfer-learned disease features are extracted from disease-relevant bio-signals according to the codebook without any medical domain knowledge, where both the disease-irrelevant data and the disease-relevant bio-signals are time-series data. Supervised learning is performed based on the transfer-learned disease features to train the classifier for disease detection.

18 Claims, 9 Drawing Sheets

(56) References Cited

U.S. PATENT DOCUMENTS

| | | | | |
|---|---|---|---|---|
| 8,452,063 | B2* | 5/2013 | Wojton | A61B 5/444 382/128 |
| 8,594,398 | B2* | 11/2013 | Beymer | A61B 8/08 382/128 |
| 8,731,248 | B2* | 5/2014 | Li | G06K 9/00281 382/117 |
| 2012/0179055 | A1* | 7/2012 | Tamil | A61B 5/0452 600/509 |
| 2017/0032221 | A1* | 2/2017 | Wu | G06K 9/6227 |

OTHER PUBLICATIONS

Schetinin, A Learning Algorithm for Evolving Cascade Neural Networks, Neural Processing Letters 17: 21-31, 2003.*

Cheerla et al, Automatic Melanoma Detection Using Multi-Stage Neural Networks, International Journal of Innovative Research in Science, Engineering and Technology, vol. 3, Issue 2, Feb. 2014.*

Oquab, M., Bottou, L., Laptev, I., and Sivic, J. Learning and transferring mid-level image representations using convolutional neural networks. In Proceedings of the IEEE Conference on Computer Vision and Pattern Recognition, pp. 1717-1724, 2014.*

Shie et al., "Transfer representation learning for medical image analysis," 37th Annual International Conference of the IEEE Engineering in Medicine and Biology Society, Aug. 25-29, 2015, pp. 1-4.

Shie et al., "A hybrid feature-based segmentation and classification system for the computer aided self-diagnosis of otitis media," 36th Annual International Conference of the IEEE Engineering in Medicine and Biology Society (EMBC), Aug. 26-30, 2014, pp. 1-4.

* cited by examiner

METHOD, ELECTRONIC APPARATUS, AND COMPUTER READABLE MEDIUM OF CONSTRUCTING CLASSIFIER FOR DISEASE DETECTION

CROSS-REFERENCE TO RELATED APPLICATION

This application is a continuation-in-part application of and claims the priority benefit of U.S. prior application Ser. No. 14/857,820, filed on Sep. 18, 2015, now pending. This application also claims the priority benefit of U.S. provisional application Ser. No. 62/198,145, filed on Jul. 29, 2015. The entirety of each of the above-mentioned patent applications is hereby incorporated by reference herein and made a part of this specification.

TECHNICAL FIELD

The disclosure relates to a method, an electronic apparatus, and a computer readable medium of constructing a classifier for disease detection.

BACKGROUND

A bio-signal refers to any infoimative time-series signal in living beings and is usually continually measured in electrical voltage levels. Some well-known medical applications of bio-signals include Electrocardiogram (ECG), Electroencephalogram (EEG), Electromyogram (EMG), Electrooculography (EOG) and Photoplethysmogram (PPG). In clinical practice, cardiologists are able to make diagnoses in heart diseases using ECG. Some helpful features to discriminate the cardiac abnormalities include the presence, duration and the location of the PQRST waves.

FIG. 1A shows the ECG of a healthy normal heart. It is noted that three deflections, P-QRS-T complexes, follow in this order and are easily differentiable. The beat rhythm is paced between 60 and 100 per minute at rest. In contrast, atrial fibrillation (AF) is one of the most common heart diseases and is characterized by the irregular fluctuation in the ECG baseline. Although the ECG baseline fluctuation is rapid and irregular, the QRS complex is usually normal. FIG. 1B illustrates this disease. Atrial flutter (AFL) is another example of abnormal heart rhythm activities. This disease is often characterized by the disappearance of the interval between the end of T-wave and beginning of P-wave. The flutter wave frequency is between 220 and 300 beats per minute and the heart beat rate is usually over 100 per minute. FIG. 1C depicts this type of heart rhythm behavior.

In practice, electroencephalogram can provide support for and help the epilepsy diagnosis and underlying epilepsy syndrome classification. There are four main types of waves in EEG: alpha, beta, theta and delta. These four waves are shown in FIG. 2A. For a normal awake person, the EEG consists of mainly alpha and some beta activities. In epileptiform activity, sharp and spike waves are observed. FIG. 2B and FIG. 2C illustrate the EEG waves in normal condition and in epileptiform activity, respectively.

Specifying aforementioned abnormalities involves ingenious heuristics and domain expertise. Unfortunately, even an expert cannot comprehensively enumerate all fundamental features (or representation) of all abnormalities. Thus, the model-based approach, which attempts to encode all knowledge in a model, cannot work effectively. In contrast to the model-based approach, the data-driven approach learns fundamental features from a large volume of data. Unfortunately, developing a good bio-signal analyzer or disease-diagnosis classifier requires a substantial amount of labeled training data. It is both laborious and expensive to obtain many labeled medical examples of any given tasks in medical analysis. For instance, a typical labeled ECG dataset is in the order of hundreds, far from the desired volume of millions or even tens of millions. Under such constraint, even the data-driven approach may fail to learn succinct feature representations.

SUMMARY OF THE DISCLOSURE

Accordingly, the disclosure is directed to a method, an electronic apparatus, and a computer readable medium of constructing a classifier for disease detection, which provides an approach to construct a robust classifier with high classification accuracy.

According to one of the exemplary embodiments, the disclosure is directed to a method of constructing a classifier for disease detection. The method includes at least but not limited to the following steps. A codebook of representative features is constructed based on a plurality of disease-irrelevant data. A plurality of transfer-learned disease features are then extracted from a plurality of disease-relevant bio-signals according to the codebook, wherein both the disease-irrelevant data and the disease-relevant bio-signals are time-series data. Supervised learning is performed based on the transfer-learned disease features to train the classifier for disease detection.

According to one of the exemplary embodiments, the disclosure is directed to an electronic apparatus. The electronic apparatus includes at least, but not limited to, a storage device, a communication device, and a processor, where the processing unit is coupled to the storage device and the communication device. The storage device is configured to record modules, and the processing unit is configured to access and execute the modules recorded in the storage device. The modules include a codebook construction module, a feature extraction module, and a feature classification module. The codebook construction module constructs a codebook of representative features based on a plurality of disease-irrelevant data obtained via the communication device. The feature extraction module extracts a plurality of transfer-learned disease features from a plurality of disease-relevant bio-signals obtained from at least one bio-sensing device via the communication device according to the codebook. The feature classification module performs supervised learning based on the transfer-learned disease features to train the classifier for disease detection.

According to one of exemplary embodiments, the disclosure is also directed to a non-transitory computer readable medium, which records computer program to be loaded into an electronic apparatus to execute the steps of the aforementioned method of constructing a classifier for disease detection. The computer program is composed of a plurality of program instructions (for example, an organization chart, establishing program instruction, a table approving program instruction, a setting program instruction, and a deployment program instruction, etc), and these program instructions are loaded into the electronic apparatus and executed by the same to accomplish various steps of the method of constructing a classifier for disease detection.

In view of the aforementioned descriptions, while the amount of labeled bio-signals for conducting statistical analysis is limited, a codebook of representative features is constructed based on disease-irrelevant data. Transfer-learned disease features are extracted from disease-relevant bio-signals according to the codebook, and the classifier for disease detection is trained by performing supervised learning based on the transfer-learned disease features. The disclosure not only mitigates the lack of labeled data problem and remedies the lack of domain knowledge to extract features, but also provides an approach to construct a robust classifier for disease detection with high classification accuracy.

In order to make the aforementioned features and advantages of the present disclosure comprehensible, preferred embodiments accompanied with figures are described in detail below.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DESCRIPTION OF THE EMBODIMENTS

There are two major challenges to overcome when developing a classifier to perform automatic disease diagnosis. First, the amount of labeled medical data is typically very limited, and a classifier cannot be effectively trained to attain high disease-detection accuracy. Second, medical domain knowledge is required to identify representative features in data for detecting a disease. Most computer scientists and statisticians do not have such domain knowledge. The main concept of the disclosure is to develop disease classifiers by adopting "transfer representation learning", which transfers knowledge learned in one or more source domains that may be unrelated to the medical analysis tasks in semantics, but similar in their low-level representations.

Specifically, time-series data such as ECG, sensory, motion, music, speech, natural sound, or artificial noise is constructed on similar fundamental time-series elements. For instance, in musical pitch C note, subsubcontra is around 8.18 Hz and four-lined is around 2093 Hz. In speech, the first three vowel formant frequencies for '/i/' vowel are 280 Hz, 2250 Hz and 2890 Hz. In activity tracking, a steady pace of 180 steps per minute corresponds to about 3 Hz. Based on the above, a huge volume of various time-series data is used to find those fundamental time-series elements and accordingly construct a codebook. That codebook can then be used to encode disease-relevant bio-signals such as ECG. Once the codebook has been constructed, ECG data can be encoded into representation vectors according to the codebook, and a supervised learning approach can be employed to develop an ECG classifier based on the encoded representation vectors.

Figure 1A:
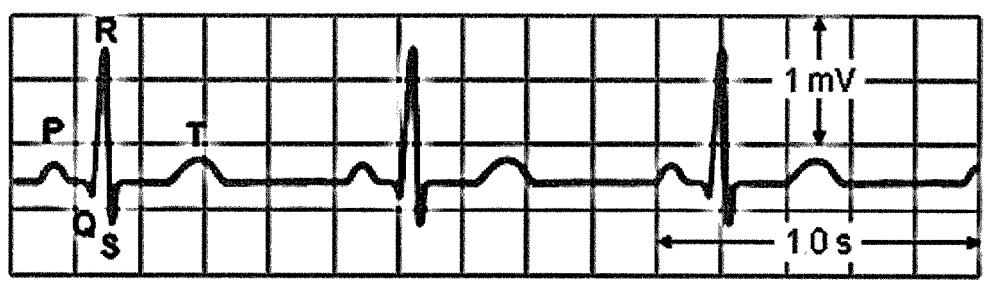
FIG. 1A to FIG. 1C illustrate the ECGs detected from a healthy normal heart and a heart with atrial fibrillation (AF) and atrial flutter (AFL).
Figure 1B:
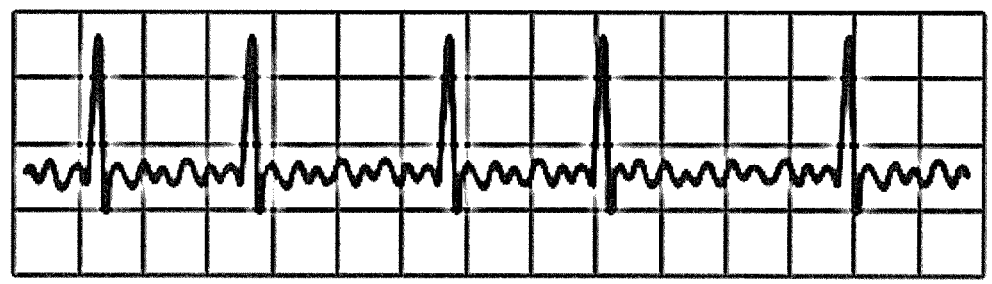
Figure 1C:
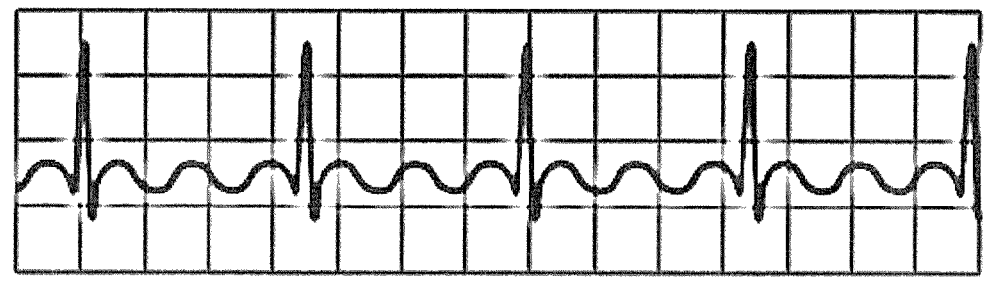
Figure 2A:
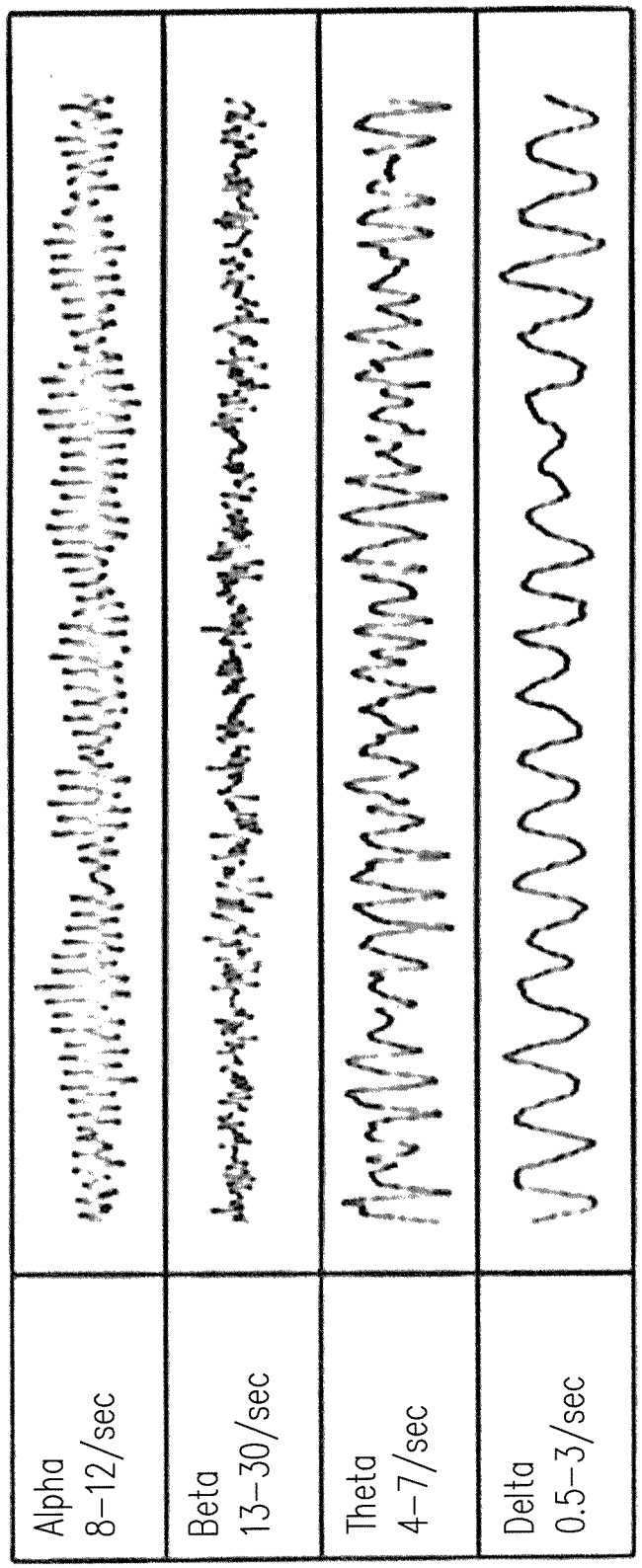
FIG. 2A to FIG. 2C illustrate main types of EEG waves and the EEG waves in normal condition and in epileptiform activity.
Figure 2B:
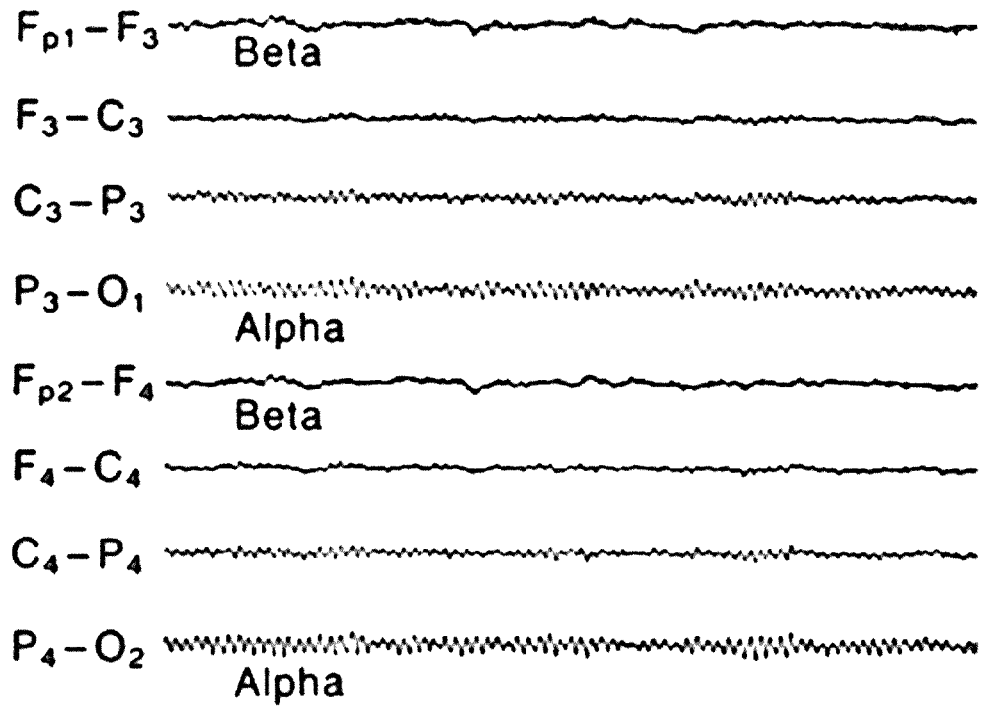
Figure 2C:
Figure 3:
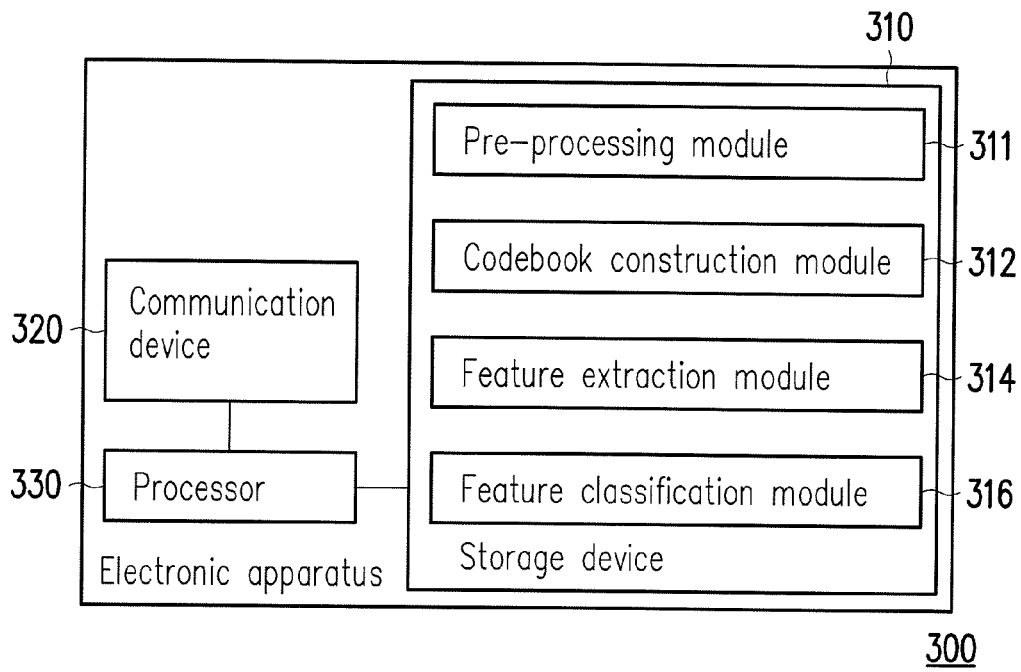
FIG. 3 illustrates a schematic diagram of an electronic apparatus of constructing a classifier for disease detection in accordance with one of the exemplary embodiments of the disclosure.

FIG. 3 illustrates a schematic diagram of a proposed electronic apparatus of constructing a classifier for disease detection in accordance with one of the exemplary embodiments of the disclosure. All components of the electronic apparatus and their configurations are first introduced in FIG. 3. The functionalities of the components are disclosed in more detail in conjunction with FIG. 4.

Referring to FIG. 3, an exemplary electronic apparatus 300 includes a storage device 310, a communication device 320, and a processor 330, where the processor 330 is coupled to the storage device 310 and the communication device 320. The electronic apparatus 300 may be a personal computer, a laptop computer, a server computer, a tabular computer, a smart phone, a workstation, or other types of computing apparatuses or platforms.

The storage device 310 may be one or a combination of a stationary or mobile random access memory (RAM), a read-only memory (ROM), a flash memory, a hard drive or other various forms of non-transitory, volatile, and non-volatile memories. The storage device 310 is configured to record a plurality of modules executable by the processor 330. The modules include a data pre-processing module 311, a codebook construction module 312, a feature extraction module 314, and a feature classification module 316. The modules may be loaded into the processor 330 for constructing a classifier for disease detection.

The communication device 320 may be an Ethernet card, an RS-232 port, a USB port, an 802.11 card, a 3G wireless modem, a 4G wireless modem, or other wired or wireless interfaces known to the person skilled in the art. The communication device 320 allows the electronic apparatus 300 to exchange data with external devices.

The processor 330 may be, for example, a central processing unit (CPU) or other programmable devices for general purpose or special purpose such as a microprocessor, a digital signal processor (DSP), a graphical processing unit (GPU), a programmable controller, an application specific integrated circuit (ASIC), a programmable logic device (PLD) or other similar or a combination of aforementioned components. The processor 330 is capable of accessing and executing the modules recorded in the storage device 310 and would be used to perform the method of constructing a classifier for disease detection as proposed.

Figure 4:
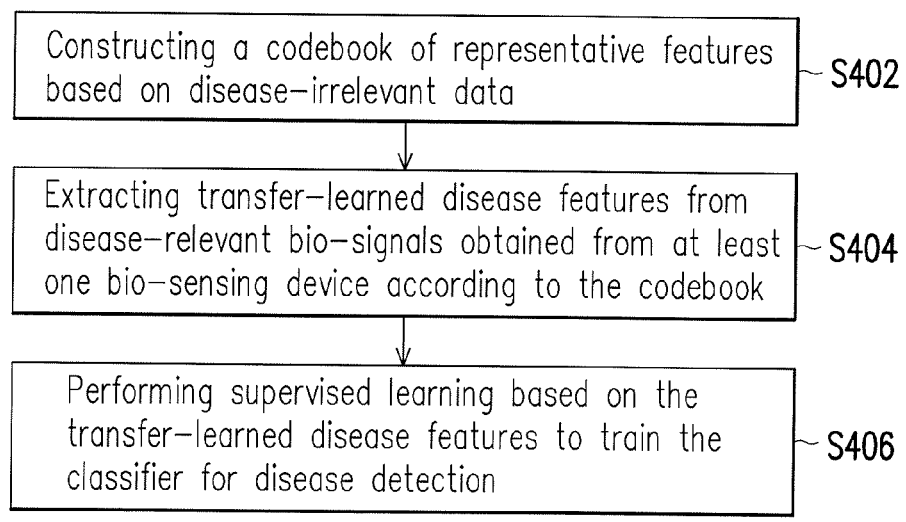
FIG. 4 illustrates a flowchart of a method of constructing a classifier for disease detection in accordance with one of the exemplary embodiments of the disclosure.

FIG. 4 illustrates a flowchart of a method of constructing a classifier for disease detection in accordance with one of the exemplary embodiments of the disclosure. The steps of FIG. 4 could be implemented by the proposed electronic apparatus 300 as illustrated in FIG. 3.

Referring to FIG. 4, the data pre-processing module 311 pre-processes raw disease-irrelevant data obtained via the communication device 320 including transforming the raw disease-irrelevant data into codebook input vectors, and the codebook construction module 312 constructs a codebook of representative features based on the pre-processed disease-irrelevant data (Step S402). The raw disease-irrelevant data may undergo filtering, resampling, interpolation, frequency-domain transfonaation and time-frequency transformation through the pre-processing module 311. It is noted that all kinds of time-series data share the same fundamental layer of representation, and the presentation learned from disease-inelevant data can be used to represent disease-relevant data. Herein, the time-series data irreverent to disease is associated with a classifier to be constructed. In detail, while the amount of labeled medical data for conducting statistical analysis is typically limited, the codebook construction module 312 would perform representation learning, e.g. deep learning, on time-series data which is typically very large in volume to be effective. For example, the codebook construction module 312 may obtain the disease-irrelevant data from an audio database, which includes a huge amount of audio signals with various frequencies such as natural sounds, artificial noise, speech sounds and music, or from an activity tacking database that contains a huge amount of sensor signals from various forms of activities. In other examples, the codebook construction module 312 may also obtain the disease-irrelevant data from other time-series sources, which is not limited herein. The codebook construction module 312 would construct the codebook based on such large amount of disease-irrelevant data and representation learning methods with absolutely no medical domain knowledge. In other words, no domain expertise is involved in identifying any features for the disease detection at this stage.

In machine learning, representation learning refers to a set of techniques that learn useful features or representations from the transfoimation of input raw data that can be easily utilized in building classifiers or other predictors. It deals with how to represent features in an input data as numerical vectors, which are known as feature descriptors. In audio domain, the feature descriptors would possess the ability to deal with audio transformations such as sound frequency, loudness, pitch, or timbre variations to some extent. In one exemplary embodiment, the codebook construction module 312 would learn the feature representation of the disease-irrelevant data by leveraging a neural-network-based approach or an energy-based approach. The models used in the neural-network-based approach and the energy-based approach would be referred to as "a first representation learning model" and "a second representation learning model" respectively below.

In one neural-network-based approach, a deep convolutional neural network (CNN) model which achieves remarkable improvement in classifying images, audio, and speech data may be utilized as the first representation learning model. For example, AlexNet, a variant of deep CNN model, may be used. AlexNet contains eight layers of neurons, where the first five layers are convolutional, and the remaining three layers are fully-connected. Different layers would represent different levels of abstraction concepts. An autoencoder, which automatically learns features from unlabelled data, may be used in another neural-network-based approach. For example, the sparse autoencoder, which is a variant of autoencoder and imposes sparsity constraints during the learning process, may be used. The sparsity constraint is typically set to a small value close to zero. In other words, the average activation of each hidden neuron is nearly zero. A recunent neural network (RNN) which possesses dynamic temporal behavior through directed cycle connections between neurons. The internal memory allows it to learn the arbitrary sequences of inputs. For example, long short term memory (LSTM) network, a variant of RNN model, may be used. Deep LSTM topology works effectively with long time-sequence delays and signals with a mix of low and high frequency components.

An energy-based approach may exploit a Restricted Boltzmann machine (RBM), which can learn a probability distribution over its set of inputs. For example, a deep belief network (DBN), which stacks multiple RBMs or autoencoders and trains the stacked RBMs or autoencoders in a greedy manner, may be used as the second representation learning model. That is, the second representation learning model would include at least one hidden layer having multiple hidden units. The activation values of stacked autoencoders of the inner layers in the first representation learning model or the probabilistic values of the hidden units in the second representation learning model can be used as the representative features of the input data (i.e. disease-irrelevant data).

Next, the feature extraction module 314 extracts transfer-learned disease features from a plurality of disease-relevant bio-signals obtained via the communication device 320 according to the codebook (Step S404), in which both the disease-irrelevant data and the disease-relevant bio-signals are time-series data. In detail, each of the disease-relevant bio-signals is measured by a bio-sensing device and used as reference for professionals to diagnose disease. Such bio-sensing device could be a sensor or an instrument for disease examination such as heart rate monitor, heart sound detector or phonocardiogram (PCG) sensor, electrocardiogram (ECG/EKG) machine, electroencephalogram (EEG) sensor, electromyogram (EMG) sensor, electrooculography (BOG) sensor, or photoplethysmogram (PPG) sensor. The feature extraction module 314 may obtain the disease-relevant bio-signals from one or more databases of a clinical system, from the internet, directly from one or more bio-sensing devices, or any other sources as long as the obtained bio-signals have been diagnosed and labeled. In other words, the bio-signals are considered as labeled data and are directly associated with the classifier to be constructed. For example, if the classifier is used for heart disease detection based on ECG, the disease-relevant bio-signals could be ECG measured by ECG machine and other bio-signals may be considered as disease-irrelevant data. The feature extraction module 314 would use the learned features from a large amount of the disease-irrelevant data to describe the disease-relevant bio-signals. Hence, the feature extraction module 314 would be considered as an encoder, which captures generic features (i.e. the transfer-learned disease features) of the disease-relevant bio-signals in a vector form by referencing the codebook.

In an exemplary embodiment in which the codebook is constructed based on a neural network, each disease-relevant bio-signal is first input to the first representation learning model. The information in each bio-signal such as its representations and features would propagate through the layers (i.e. from an input layer to an output layer through inner layers). Each layer is a weighted combination of the previous layer and stands for a feature representation of the input bio-signal. Since the computation is hierarchical, higher layers intuitively represent high abstraction concepts. For bio-signals, the neurons from lower levels describe rudimental perceptual elements such as fundamental waves or frequencies, while higher layers represent composite parts such as P-waves, QRS-waves and T-waves in ECG. In an exemplary embodiment in which the codebook is constructed based on a deep belief network, the feature extraction module 314 would extract transfer-learned features of the bio-signals in a similar fashion.

To further improve the classification accuracy, especially for heart disease classification whose signals are often with variance, data pre-processing module 311 could be utilized to perform a pre-preprocessing step prior to feature extraction. To be specific, the pre-processing module 311 may first filter and segment the disease-relevant bio-signals to generate corresponding segmented signals, and pass the resulting input vectors to the feature extraction module 314 to extract the transfer-learned disease features from the segmented signals thereafter.

Once the feature extraction module 314 has extracted the transfer-learned disease features, the feature classification module 316 performs supervised learning based on the transfer-learned disease features to train the classifier for disease detection (Step S406). In machine learning, supervised learning refers to inferring a model from labeled data, and the inferred model can predict answers of unseen data. In an exemplary embodiment, the feature classification module 316 may employ a Support Vector Machine (SVM) classifier as the classifier for disease detection, where the SVM classifier is considered as an effective supervised learning tool used in classification. After the classifier for disease detection is constructed, in one scenario where a personal bio-sensing device is available, preliminary diagnosis could be performed at home, and medical attention could be sought.

For instance, the classifier for heart disease detection could be installed in an ECG machine. After a new ECG signal is detected by the ECG machine, the installed classifier would classify whether the new ECG signal implies any heart disease, and the ECG machine would output the classification result by, for example, a display. In another instance, the classifier for heart disease detection could be installed in a cloud server or an external electronic apparatus, and the ECG machine would transmit the new ECG signal to the classifier and receive the classification result from the classifier via wired or wireless transmission. In another instance, the new ECG signal along with the classification result may be transmitted to the medical database. Similar scenario could also apply to other bio-sensing devices.

In an exemplary embodiment, the ECG signals may be fused with concurrently detected heart sound signals to train the classifier for heart disease detection. Specifically, in case that the codebook is constructed based on audio signals, the codebook is more ideal for extracting features from the heart sound signals due to similar attributes and the features of the ECG signals having matched timestamps with the features of the heart sound signals may be fused to train the classifier for heart disease detection. As a result, a robust disease classifier with high classification accuracy may be obtained.

Figure 5A:
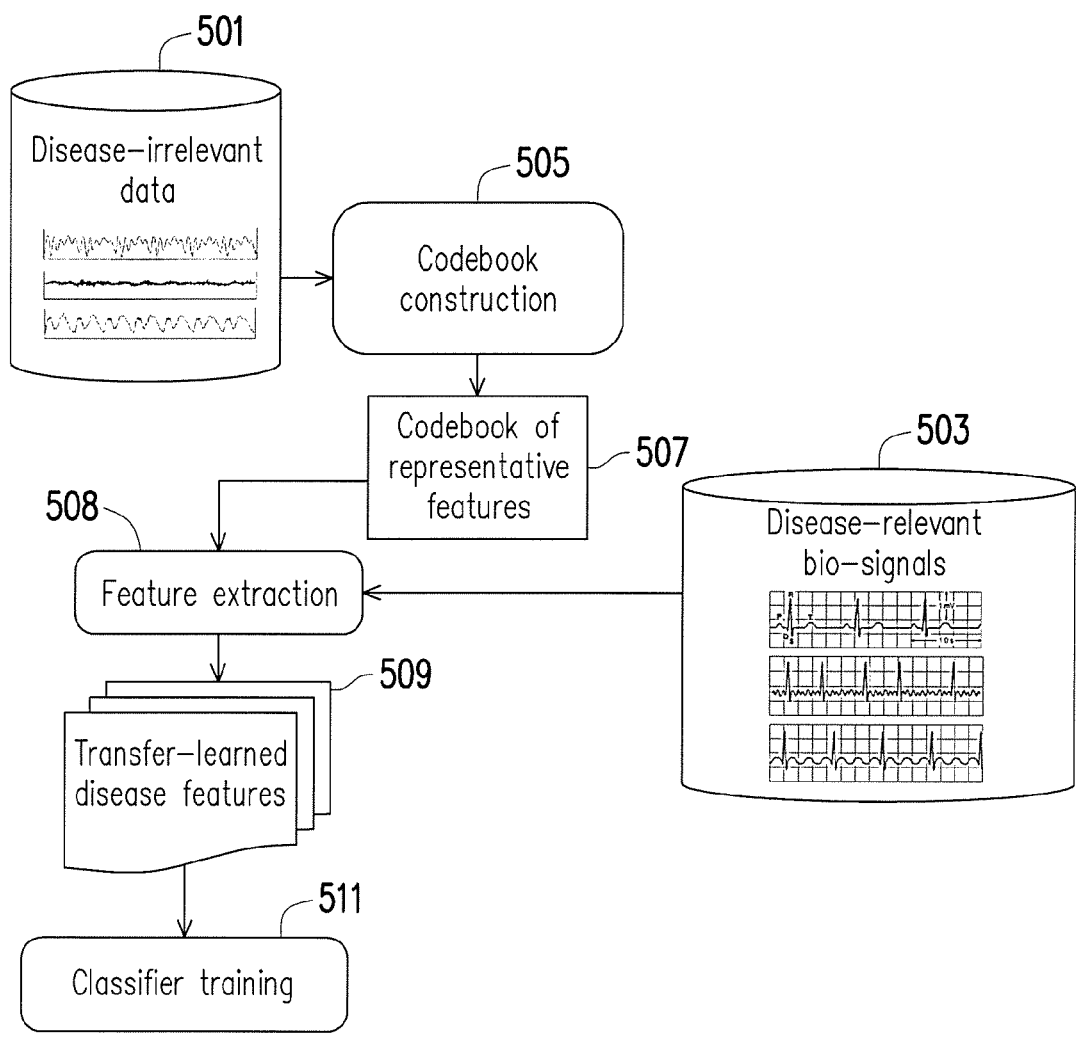
FIG. 5A illustrates a functional block diagram of a method of constructing a classifier for disease detection in accordance with one of the exemplary embodiments of the disclosure.
Figure 5B:
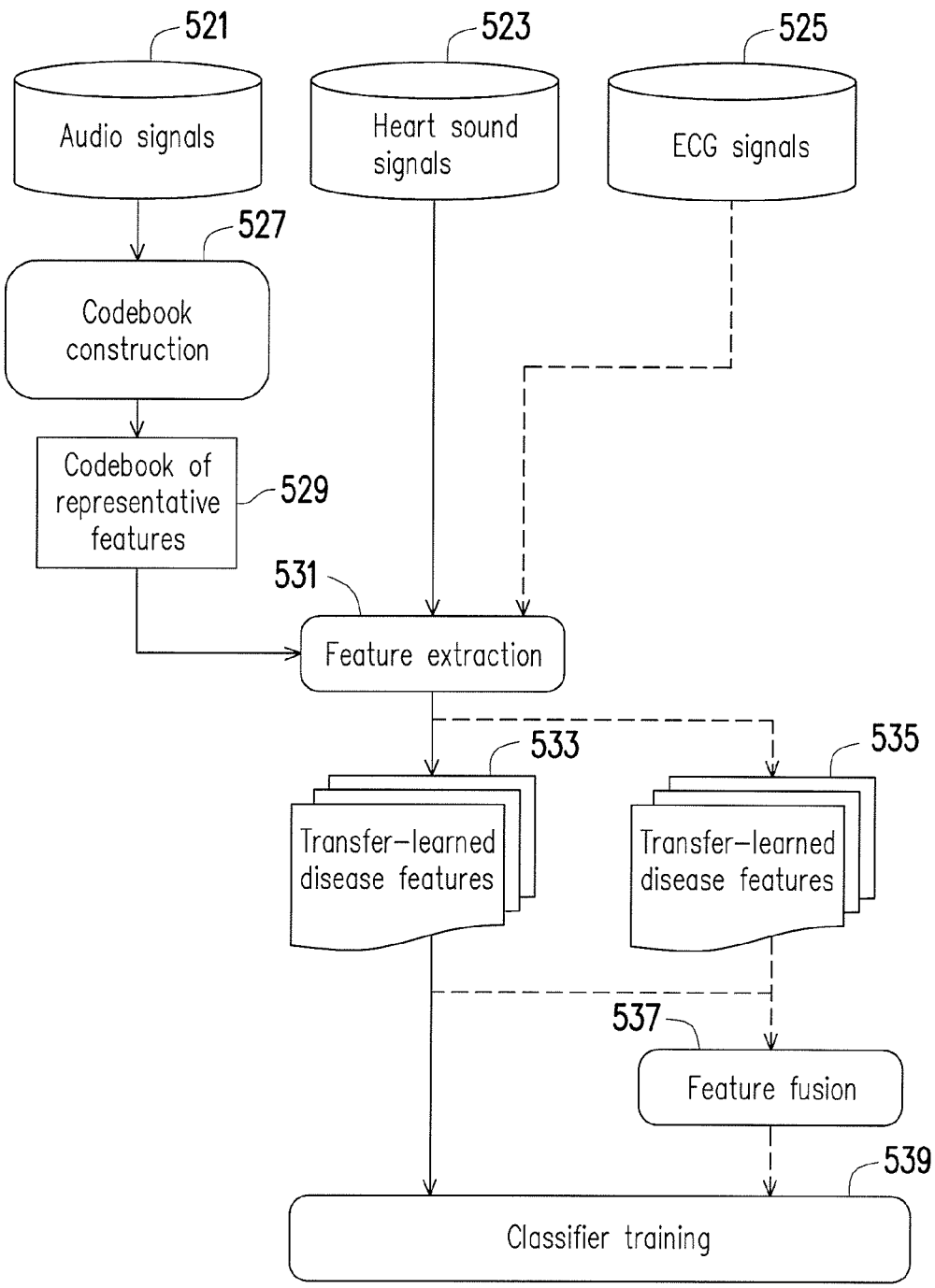
FIG. 5B illustrates a functional block diagram of a method of constructing a classifier for disease detection in accordance with one of the exemplary embodiments of the disclosure.

The proposed method of constructing a classifier for disease detection could be summarized by FIG. 5A and FIG. 5B in terms of functional block diagrams in accordance with one of the exemplary embodiments of the disclosure.

Referring to FIG. 5A, codebook construction 505 is performed by using representation learning methods to generate a codebook of representative features 507 based on a large amount of disease-irrelevant data 501. Feature extraction 508 is performed on disease-relevant bio-signals 503 to obtain transfer-learned disease features 509. The classifier training 511 is performed based on the transfer-learned disease features.

Referring to FIG. 5B, codebook construction 527 is performed by using representation learning methods to generate a codebook of representative features 529 based on a large amount of audio signals 521. Feature extraction 531 is respectively performed on the heart sound signals 523 and the ECG signals 525 according to the codebook of representative features 529 so as to obtain transfer-learned disease features 533 of the heart sound signals 523 and transfer-learned disease features 535 of the ECG signals 525. Feature fusion 537 is performed by concatenating the transfer-learned disease features 533 and the transfer-learned disease features 535 to form a plurality of fused feature vectors. The classifier training 539 is performed on the fused feature vectors to train the classifier for disease detection.

To further improve the classification accuracy, two feature fusion schemes are provided below for classification construction, where the learned transfer-features are combined with heuristic features.

Figure 6:
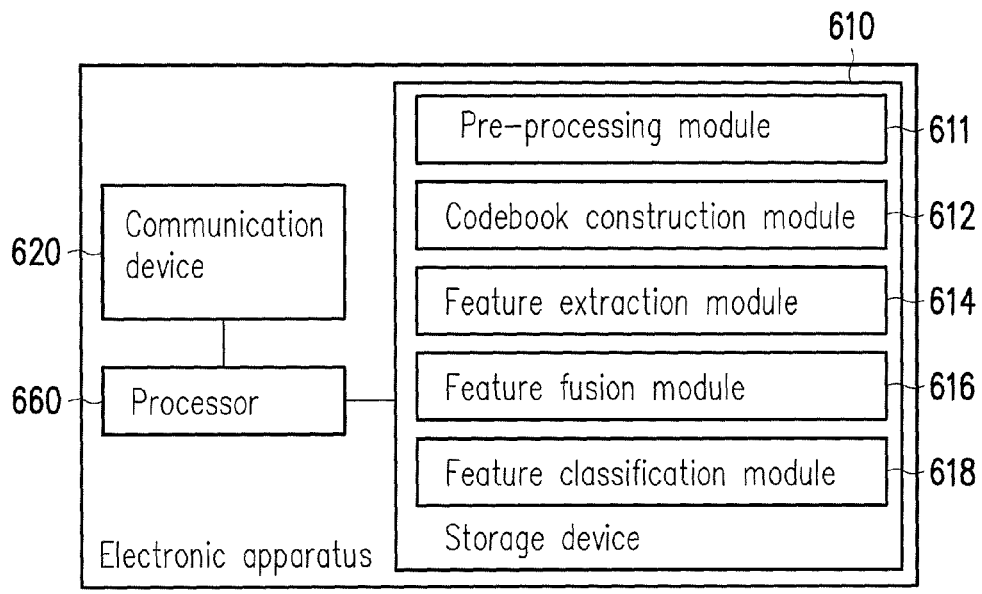
FIG. 6 illustrates a schematic diagram of an electronic apparatus of constructing a classifier for disease detection in accordance with another exemplary embodiment of the disclosure.

FIG. 6 illustrates a schematic diagram of a proposed electronic apparatus of constructing a classifier for disease detection in accordance with another exemplary embodiment of the disclosure.

Referring to FIG. 6, an electronic apparatus 600 includes a storage unit 610, a communication interface 620, and a processor 630, where the processor 630 is coupled to the storage unit 610 and the communication interface 620, where similar components to FIG. 3 are designated with similar numbers having a "6" prefix. The only difference is that the modules recorded in the storage unit 610 include a pre-processing module 611, a codebook construction module 612, a feature extraction module 614, a feature fusion module 616, and a feature classification module 618. The modules may be loaded into the processor 620 for constructing a classifier for disease detection.

Figure 7:
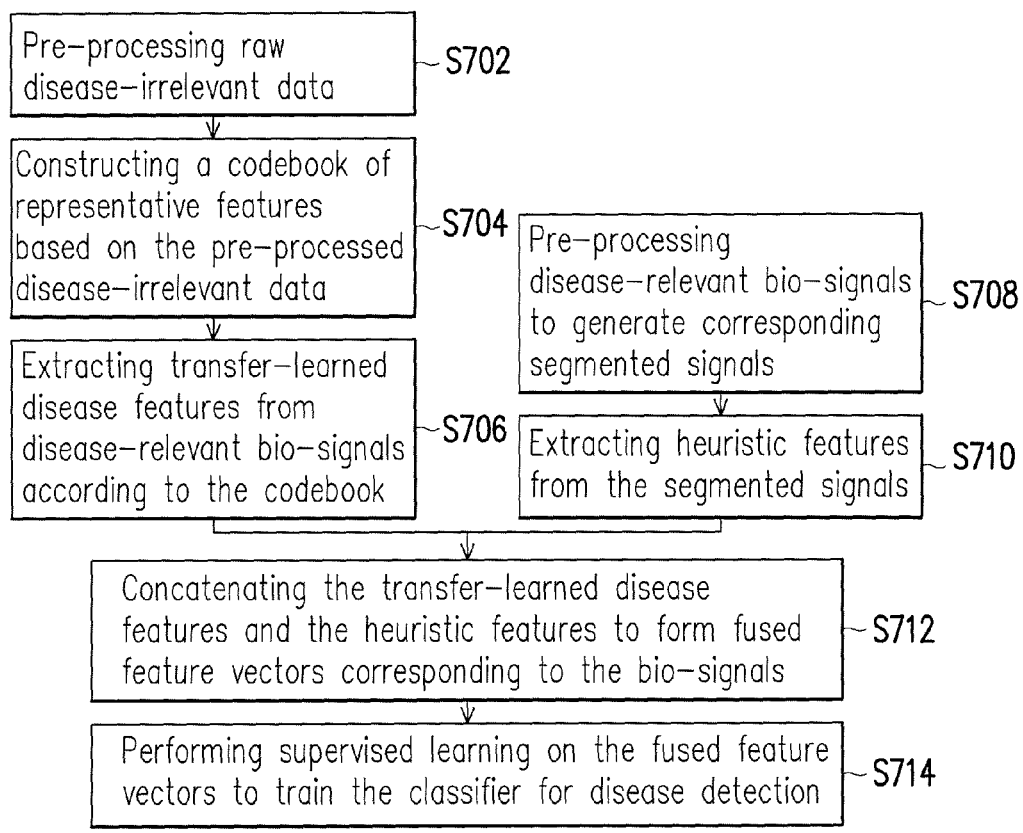
FIG. 7 illustrates a flowchart of a method of constructing a classifier for disease detection in accordance with another exemplary embodiment of the disclosure.

FIG. 7 illustrates a flowchart of a method of constructing a classifier for disease detection in accordance with another exemplary embodiment of the disclosure. The steps of FIG. 7 could be implemented by the proposed electronic apparatus 600 as illustrated in FIG. 6.

Referring to FIG. 6, the pre-processing module 611 of the electronic apparatus 600 pre-processes raw disease-irreverent data including filtering and transfoiming the raw disease-irreverent data into input vectors prior to further processing (Step S702), and then the codebook construction module 612 constructs a codebook of representative features based on the pre-processed disease-irreverent data (Step S704). Next, the feature extraction module 614 of the electronic apparatus 600 extracts transfer-learned disease features from disease-relevant bio-signals obtained from a medical database via the communication interface 620 according to the codebook (Step S706). In the same manner as described previously with respect to the exemplary embodiment in FIG. 5, the detailed descriptions of Steps S702 to S706 will not be repeated herein.

In the present exemplary embodiment, the feature extraction module 614 further extracts important visual cues related to visual symptoms in the disease-relevant bio-signals. To be specific, the pre-processing module 611 first pre-processes disease-relevant bio-signals, including filtering, segmenting and transforming the disease-relevant bio-signals, to generate corresponding segmented signals (Step S708). Then, the feature extraction module 614 extracts heuristic features from the segmented signals (Step S710). The heuristic features herein refer to certain important visual cues that describe visual symptoms (e.g. morphological characteristics or peak-to-peak intervals, etc.) of disease-relevant bio-signals. The morphological characteristics may refer to characteristics of waveform of electrical signals such as sine wave or triangle wave, or may refer to characteristics of waveform of the disease-relevant bio-signals such as P-waves, QRS-waves and T-waves in ECG signal.

Once the feature extraction module 614 completes extracting transfer-learned disease features and extracting the heuristic features from each of the disease-relevant bio-signals, the feature fusing module 616 concatenates the transfer-learned disease features and the heuristic features to form fused feature vectors of each of the bio-signals (Step S712), and the feature classification module 618 performs supervised learning on the fused feature vectors to train the classifier for disease detection (Step S714). In an exemplary embodiment, the feature classification module 618 may also employ a SVM classifier as the classifier for disease detection similar to Step S506.

Figure 8:
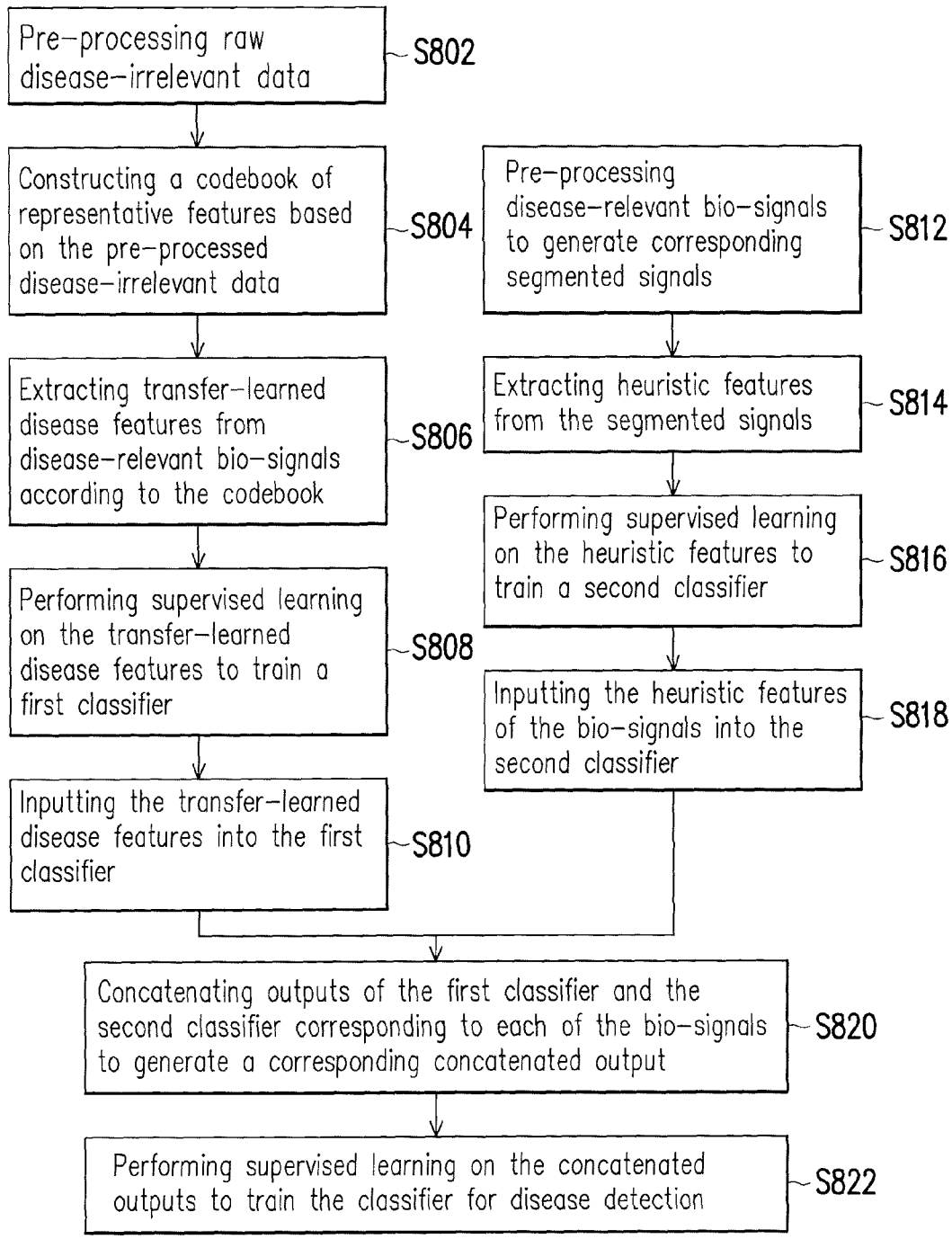
FIG. 8 illustrates a flowchart of a method of constructing a classifier for disease detection in accordance with another exemplary embodiment of the disclosure.

The fusion scheme introduced in FIG. 7 may be referred to as a feature-level fusion, where the feature fusion is performed by concatenating two feature sets. In another exemplary embodiment, a classifier-level fusion may be performed. To be specific, FIG. 8 illustrates a flowchart of a method of constructing a classifier for disease detection in accordance with another exemplary embodiment of the disclosure. The steps of FIG. 8 could be implemented by the proposed electronic apparatus 600 as illustrated in FIG. 6.

Referring to FIG. 8, the pre-processing module 611 of the electronic apparatus 600 pre-processes raw disease-irreverent data, including filtering and transforming the raw disease-irreverent data into input vectors, prior to further processing (Step S802), and then the codebook construction module 612 of the electronic apparatus 600 constructs a codebook of representative features based on the pre-processed disease-irreverent data (Step S804). The feature extraction module 614 of the electronic apparatus 600 extracts transfer-learned disease features from disease-relevant bio-signals obtained from a medical database via the communication interface 620 according to the codebook (Step S806).

On the other hand, the pre-processing module 611 pre-processes disease-relevant bio-signals, including filtering, segmenting and transforms the disease-relevant bio-signals, to generate corresponding segmented signals (Step S812) and then the feature extraction module 614 extracts heuristic features from the segmented signals (Step S814). In the same manner as described previously with respect to the exemplary embodiment in FIG. 7, the detailed descriptions of Step S702 to Step S708 will not be repeated herein.

In the present exemplary embodiment, a two-layer classifier fusion structure is used. In the first layer, different classifiers are trained upon different feature sets separately. Concisely, the feature fusion module 616 divides the disease-relevant bio-signals into a training set and a test set. The feature fusion module 616 performs supervised learning on the transfer-learned disease features of the training signals to train a first classifier (Step S808) and also performs supervised learning on the heuristic features of the training signals to train a second classifier (Step S816). In the present exemplary embodiment, the first classifier and the second classifier may both be a SVM classifier, and yet the disclosure is not limited thereto.

The feature fusion module 616 would combine outputs from the first layer to train the classifier in the second layer. To be specific, the feature fusion module 616 inputs the transfer-learned disease features of the disease-relevant test bio-signals into the first classifier (S810) and inputs the heuristic features of the disease-relevant test bio-signals respectively into the second classifier (Step S818). Next, the feature fusion module 616 concatenates outputs of the first classifier and the second classifier corresponding to each of the disease-relevant bio-signals (Step S820). The feature classification module 618 performs supervised learning on the concatenated outputs to train the classifier for disease detection (Step S822). In the present embodiment, the classifier in the second-layer (i.e. the classifier for disease detection) may be a SVM or random forest classifier, and yet the disclosure is not limited herein.

It is noted that in one exemplary embodiment, a classifier for disease detection may also be constructed purely based on heuristics-based features. In the present embodiment, supervised learning is performed on different heuristic features of the disease-relevant training bio-signals to train different first-level classifiers and outputs from the first-level classifiers are combined to train the classifier for disease detection. To be specific, the heuristic features of the disease-relevant test bio-signals are input into different classifiers, the outputs of the different classifiers corresponding to each of the disease-relevant test bio-signals are concatenated, and supervised learning is performed on the concatenated outputs of the different classifiers so as to train the classifier for disease detection. In the present embodiment, the classifier in the second-layer (i.e. the classifier for disease detection) may be a SVM classifier, and yet the disclosure is not limited herein.

Figure 9:
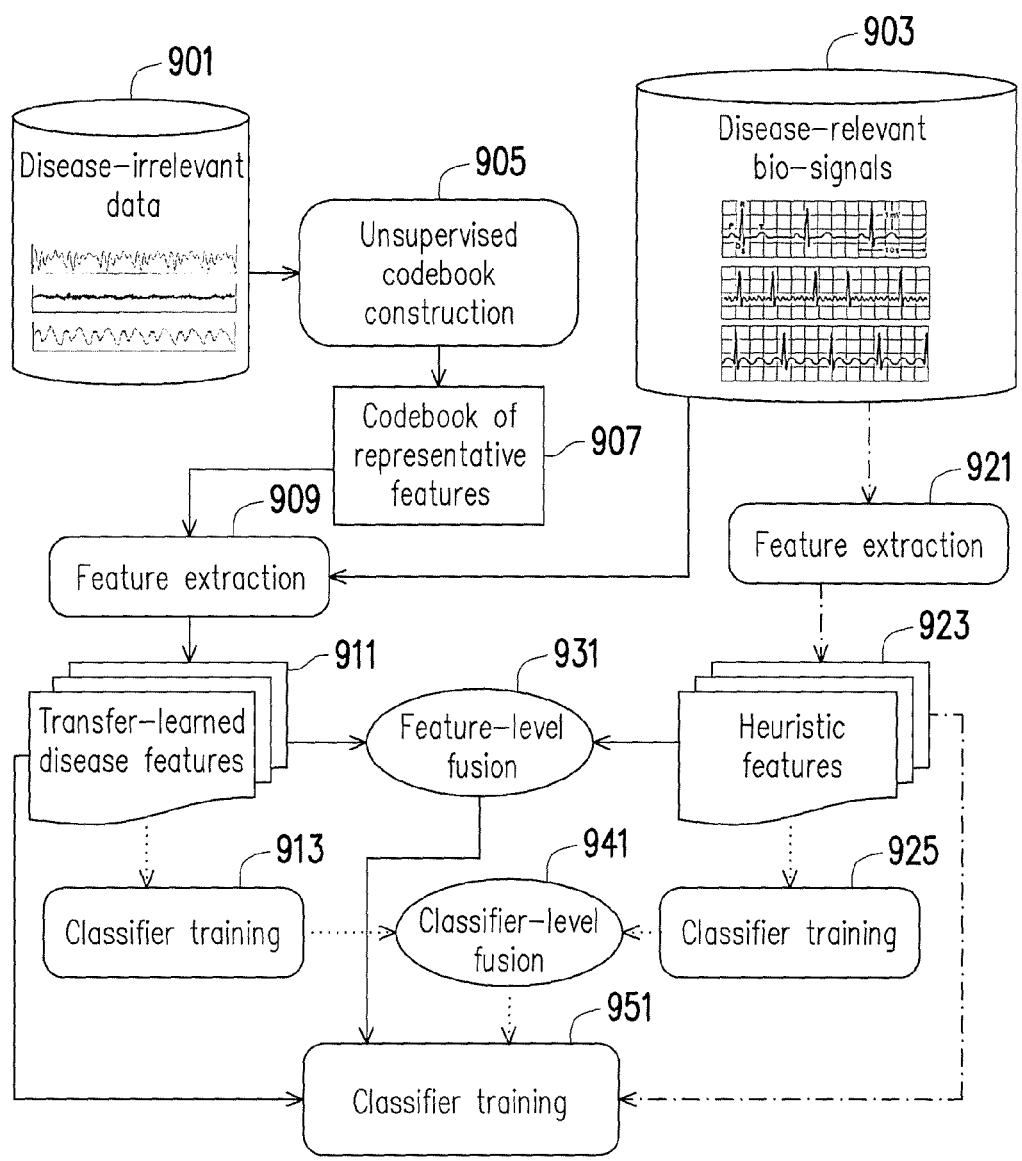
FIG. 9 illustrates a functional block diagram of a method of constructing a classifier for disease detection in accordance with one of the exemplary embodiments of the disclosure.

The proposed methods of constructing a classifier for disease detection could be summarized by FIG. 9 in terms of functional block diagrams in accordance with one of the exemplary embodiments of the disclosure. Referring to FIG. 9, several classifier construction schemes are depicted, where the transfer-learning scheme is on the left-hand side and the heuristic-based scheme is on the right-hand side.

The solid lines depict a flow for constructing a classifier only based on transfer-learned features. Unsupervised codebook construction 905 is performed based on a large amount of disease-irrelevant data 901 to generate a codebook of representative features 907. Feature extraction 909 is performed on disease-relevant bio-signals 903 to obtain transfer-learned disease features 911. Classifier training 951 is performed based on the transfer-learned disease features. On the other hand, the dash-dot lines depict a flow for constructing a classifier only based on heuristic-based features. Feature extraction 921 is performed on the disease-relevant bio-signals 903 to obtain heuristic features 923, and classifier training 951 is performed based on the heuristic features 923.

The dash lines and the dotted lines depict a flow for constructing a classifier based on transfer-learned disease features and heuristic features. Feature-level fusion 931 is performed by concatenating the transfer-learned disease features 911 and the heuristic features 923, and classifier training 951 is performed based on the outputs of the feature-level fusion 931. Classifier-level fusion 941 is performed based on the results of two classifier trainings 913 and 925 respectively corresponding to the transfer-learned disease features 911 and the heuristic features 923, and classifier training 951 is performed based on the output of the classifier-level fusion 941.

The disclosure also provides a non-transitory computer readable medium, which records computer program to be loaded into an electronic apparatus to execute the steps of the aforementioned method of constructing a classifier for disease detection. The computer program is composed of a plurality of program instructions (for example, an organization chart, establishing program instruction, a table approving program instruction, a setting program instruction, and a deployment program instruction, etc.), and these program instructions are loaded into the electronic apparatus and executed by the same to accomplish various steps of the method aforementioned method of constructing a classifier for disease detection.

In view of the aforementioned descriptions, while the amount of labeled disease-relevant bio-signals for conducting statistical analysis is limited, a codebook of representative features is constructed based on disease-irrelevant data in the disclosure. Transfer-learned disease features are extracted from disease-relevant bio-signals according to the codebook, and the classifier for disease detection is trained by performing supervised learning based on the transfer-learned disease features. The disclosure not only mitigates the lack of labeled data problem and remedies the lack of domain knowledge to extract features, but also provides an approach to construct a robust disease classifier with high classification accuracy.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims and their equivalents.

Moreover, the claims should not be read as limited to the described order or elements unless stated to that effect. In addition, use of the term "means" in any claim is intended to invoke 35 U.S.C. §612, ¶6, and any claim without the word "means" is not so intended.

What is claimed is:

1. A method of constructing a classifier for disease detection, adapted to an electronic apparatus, comprising:
    constructing a codebook of representative features based on a plurality of disease-irrelevant data, wherein the disease-irrelevant data is non-medical data;
    extracting a plurality of transfer-learned disease features from a plurality of disease-relevant bio-signals according to the codebook, wherein both the disease-irrelevant data and the disease-relevant bio-signals are time-series data, and the disease-irrelevant data comprises a plurality of audio signals; and
    performing supervised learning based on the transfer-learned disease features to train the classifier for disease detection,
    wherein the steps of extracting a plurality of transfer-learned disease features from the plurality of disease-relevant bio-signals according to the codebook and performing supervised learning based on the transfer-learned disease features to train the classifier for disease detection comprise:
        extracting a plurality of first transfer-learned disease features from a plurality of heart sound signals according to the codebook;
        extracting a plurality of second transfer-learned disease features from a plurality of electrocardiac (ECG) signals according to the codebook;
        concatenating the first transfer-learned disease features and the second transfer-learned disease features to form a plurality of fused feature vectors; and
        performing supervised learning on the fused feature vectors to train the classifier for disease detection.

2. The method according to claim 1, wherein the step of constructing the codebook of the representative features based on the disease-irrelevant data comprises:
    constructing the codebook of the representative features based on the disease-irrelevant data by using a first representation learning model, wherein the first representation learning model comprises a plurality of layers of neurons, wherein the layers comprise at least one inner layer, and wherein activation values of the inner layers corresponds to the representative features of the disease-irrelevant data.

3. The method according to claim 2, wherein the step of extracting the transfer-learned disease features from the disease-relevant bio-signals according to the codebook comprises:
    for each of the bio-signals:
    inputting the disease-relevant bio-signal into the first representation learning model;
    propagating information in the disease-relevant bio-signal through the layers; and
    obtaining the transfer-learned disease features of the disease-relevant bio-signal according to at least one of the inner layers.

4. The method according to claim 1, wherein the step of constructing the codebook of the representative features based on the disease-irrelevant data comprises:
    constructing the codebook of the representative features based on the disease-irrelevant data by using a second representation learning model, wherein the second representation learning model comprises a plurality of layers of units, wherein the layers comprise at least one hidden layer having a plurality of hidden units, and wherein probabilistic values of the hidden units correspond to the representative features of the disease-irrelevant data.

5. The method according to claim 4, wherein the step of extracting the transfer-learned disease features from the disease-relevant bio-signals according to the codebook comprises:
    for each of the bio-signals:
    inputting the disease-relevant bio-signal into the second representation learning model;
    propagating information in the disease-relevant bio-signal through the layers; and
    obtaining the transfer-learned disease features of the disease-relevant bio-signal according to at least one of the hidden units.

6. The method according to claim 1, further comprises:
    pre-processing a plurality of raw disease-relevant bio-signals by one or a combination of filtering, segmentation, frequency-domain transformation and time-frequency transformation to obtain pre-processed bio-signals; and
    extracting a plurality of heuristic features from the pre-processed bio-signals.

7. The method according to claim 6, wherein the step of performing supervised learning based on the transfer-learned disease features to train the classifier for disease detection, the method further comprises:

concatenating the transfer-learned disease features and the heuristic features to form a plurality of fused feature vectors corresponding to the disease-relevant bio-signals; and performing supervised learning on the fused feature vectors to train the classifier for disease detection.

8. The method according to claim 6, the step of performing supervised learning based on the transfer-learned disease features to train the classifier for disease detection further comprises:

performing supervised learning on the transfer-learned disease features to train a first classifier;

performing supervised learning on the heuristic features to train a second classifier;

inputting the transfer-learned disease features and the heuristic features of the disease-relevant bio-signals respectively into the first classifier and the second classifier; and concatenating outputs of the first classifier and the second classifier corresponding to each of the disease-relevant bio-signals to generate a corresponding concatenated output; and performing supervised learning on the concatenated outputs to train the classifier for disease detection.

9. The method according to claim 1, wherein after the step of performing supervised learning based on the transfer-learned disease features to train the classifier for disease detection, the method further comprises:

obtaining a new disease-relevant bio-signal; and classifying the new disease-relevant bio-signal by using the classifier for disease detection to generate a classification result; and outputting the classification result.

10. An electronic apparatus, comprising:

a communication device;

a storage device, recording a plurality of modules; and a processor, coupled to the communication device and the storage device, and accessing and executing the modules stored in the storage device, wherein the modules comprise:

a codebook construction module, constructing a codebook of representative features based on a plurality of disease-irrelevant data obtained via the communication device, wherein the disease-irrelevant data is non-medical data;

a feature extraction module, extracting a plurality of transfer-learned disease features from a plurality of disease-relevant bio-signals obtained from at least one bio-sensing device via the communication device according to the codebook, wherein both the disease-irrelevant data and the disease-relevant bio-signals are time-series data, and the disease-irrelevant data comprises a plurality of audio signals, wherein the feature extraction module extracts a plurality of first transfer-learned disease features from a plurality of heart sound signals according to the codebook and extracts a plurality of second transfer-learned disease features from a plurality of electrocardiac (ECG) signals according to the codebook;

a feature classification module, performing supervised learning based on the transfer-learned disease features to train the classifier for disease detection; and a feature fusing module, concatenating the first transfer-learned disease features and the second transfer-learned disease features to form a plurality of fused feature vectors, wherein the feature classification module performs supervised learning on the fused feature vectors to train the classifier for disease detection.

11. The electronic apparatus according to claim 10, wherein the codebook construction module constructs the codebook of the representative features based on the disease-irrelevant data by using a first representation learning model, wherein the first representation learning model comprises a plurality of layers of neurons, wherein the layers comprise at least one inner layer, and wherein activation values of the inner layers corresponds to the representative features of the disease-irrelevant data.

12. The electronic apparatus according to claim 11, wherein for each of the bio-signals, the feature extraction module inputs inputting the disease-relevant bio-signal into the first representation learning model, propagates information in the bio-signal through the layers, and obtains the transfer-learned disease features of the disease-relevant bio-signal according to at least one of the inner layers.

13. The electronic apparatus according to claim 10, wherein the codebook construction module constructs the codebook of the representative features based on the disease-irrelevant data by using a second representation learning model, wherein the second representation learning model comprises a plurality of layers of units, wherein the layers comprise at least one hidden layer having a plurality of hidden units, and wherein probabilistic values of the hidden units correspond to the representative features of the disease-irrelevant data, wherein for each of the bio-signals, the feature extraction module inputs the disease-relevant bio-signal into the second representation learning model, propagates information in the disease-relevant bio-signal through the layers, and obtains the transfer-learned disease features of the bio-signal according to at least one of the hidden units.

14. The electronic apparatus according to claim 10, wherein the modules further comprise:

a pre-processing module, performing one or a combination of filtering, segmentation, frequency-domain transformation and time-frequency transformation on a plurality of raw disease-irrelevant data and raw disease-relevant bio-signals to obtain pre-processed disease-irrelevant data and pre-processed bio-signals, wherein the codebook construction module constructs the codebook of representative features based on the pre-processed disease-irrelevant data; and the feature extraction module extracts a plurality of heuristic features from the pre-processed bio-signals.

15. The electronic apparatus according to claim 14, wherein the modules further comprise:

a feature fusing module, concatenating the transfer-learned disease features and the heuristic features to form a plurality of fused feature vectors corresponding to the disease-relevant bio-signals, wherein the feature classification module performs supervised learning on the fused feature vectors to train the classifier for disease detection.

16. The electronic apparatus according to claim 14, wherein the feature classification module performs supervised learning on the transfer-learned disease features to train a first classifier, performs supervised learning on the heuristic features to train a second classifier, and inputs the transfer-learned disease features and the heuristic features of the disease-relevant bio-signals respectively into the first classifier and the second classifier, wherein the modules further comprise:
a feature fusing module, concatenating outputs of the first classifier and the second classifier corresponding to each of the disease-relevant bio-signals to generate a corresponding concatenated output, wherein the feature classification module performs supervised learning on the concatenated outputs to train the classifier for disease detection.

17. The electronic apparatus according to claim 10, wherein the feature classification module obtains a new disease-relevant bio-signal from the bio-sensing device by the communication device, classifies the new disease-relevant bio-signal by using the classifier for disease detection to generate a classification result, and outputs the classification result.

18. A non-transitory computer readable medium, storing programs to be loaded into an electronic apparatus to perform steps of:
constructing a codebook of representative features based on a plurality of disease-irrelevant data, wherein the disease-irrelevant data is non-medical data;
extracting a plurality of transfer-learned disease features from a plurality of disease-relevant bio-signals according to the codebook, wherein both the disease-irrelevant data and the disease-relevant bio-signals are time-series data, and the disease-irrelevant data comprises a plurality of audio signals; and
performing supervised learning based on the transfer-learned disease features to train the classifier for disease detection,
wherein the steps of extracting a plurality of transfer-learned disease features from the plurality of disease-relevant bio-signals according to the codebook and performing supervised learning based on the transfer-learned disease features to train the classifier for disease detection comprise:
extracting a plurality of first transfer-learned disease features from a plurality of heart sound signals according to the codebook;
extracting a plurality of second transfer-learned disease features from a plurality of electrocardiac (ECG) signals according to the codebook;
concatenating the first transfer-learned disease features and the second transfer-learned disease features to form a plurality of fused feature vectors; and
performing supervised learning on the fused feature vectors to train the classifier for disease detection.

* * * * *